(12) United States Patent
Jayakody et al.

(10) Patent No.: US 9,839,715 B2
(45) Date of Patent: Dec. 12, 2017

(54) ANTI-MICROBIAL FOAMS CONTAINING POLYMER-STABILIZED SILVER NANOPARTICLES

(71) Applicant: Essentra Porous Technologies Corp., Colonial Heights, VA (US)

(72) Inventors: Chandrasiri Jayakody, Saginaw, MI (US); Anthony J. Joles, Saginaw, MI (US); Ramesh Srinivasan, Moseley, VA (US); Geoffrey M. Stoltz, Moseley, VA (US)

(73) Assignee: Porex Technologies Corporation, Colonial Heights, VA (US)

( * ) Notice: Subject to any disclaimer, the term of this patent is extended or adjusted under 35 U.S.C. 154(b) by 0 days.

(21) Appl. No.: 14/826,122

(22) Filed: Aug. 13, 2015

(65) Prior Publication Data

US 2016/0045635 A1 Feb. 18, 2016

Related U.S. Application Data

(60) Provisional application No. 62/036,672, filed on Aug. 13, 2014.

(51) Int. Cl.

| | | |
|---|---|---|
| *A61L 15/44* | (2006.01) | |
| *A61L 15/42* | (2006.01) | |
| *A61L 15/46* | (2006.01) | |
| *C08J 9/00* | (2006.01) | |
| *B29K 75/00* | (2006.01) | |
| *B29K 105/04* | (2006.01) | |
| *B29K 105/16* | (2006.01) | |
| *B29K 505/14* | (2006.01) | |
| *B29L 31/00* | (2006.01) | |
| *A61L 15/60* | (2006.01) | |

(52) U.S. Cl.
CPC ............ *A61L 15/44* (2013.01); *A61L 15/425* (2013.01); *A61L 15/46* (2013.01); *A61L 15/60* (2013.01); *C08J 9/008* (2013.01); *A61L 2300/104* (2013.01); *A61L 2300/206* (2013.01); *A61L 2300/404* (2013.01); *A61L 2400/12* (2013.01); *B29K 2075/00* (2013.01); *B29K 2105/04* (2013.01); *B29K 2105/162* (2013.01); *B29K 2505/14* (2013.01); *B29L 2031/753* (2013.01); *C08J 2375/04* (2013.01); *C08J 2375/06* (2013.01); *C08J 2375/08* (2013.01)

(58) Field of Classification Search
CPC .......... A61L 15/44; A61L 15/46; A61L 15/60; A61L 15/425; A61L 2400/12; A61L 2300/404; A61L 2300/104; A61L 2300/206; C08J 9/008; C08J 2375/04; C08J 2375/06; C08J 2375/08; B29K 2075/00; B29K 2105/04; B29K 2105/162; B29K 2505/14; B29K 2995/0037; B29L 2031/753

See application file for complete search history.

(56) References Cited

U.S. PATENT DOCUMENTS

| | | |
|---|---|---|
| 4,207,279 A | 6/1980 | Boon |
| 6,503,952 B2 | 1/2003 | Modak et al. |
| 7,482,503 B2 | 1/2009 | Gregory et al. |
| 8,183,167 B1 | 5/2012 | Delattre et al. |
| 8,852,639 B2 | 10/2014 | MacKay |
| 8,920,850 B2 | 12/2014 | Davis |
| 2010/0260824 A1* | 10/2010 | Shah ............... A01N 25/00 424/447 |
| 2012/0322903 A1* | 12/2012 | Karandikar ....... A01N 59/16 521/92 |

OTHER PUBLICATIONS

Liu et al. ("Nanocomposites of Genipin-Crosslinked Chitosan/Silver Nanoparticles—Structural Reinforcement and Antimicrobial Properties" in Macromolecular Bioscience, 2008, vol. 8, pp. 932-941).*

Liu, B-S. et al., Nanocomposites of Genipin-Crosslinked Chitosan/Silver Nanoparticles—Structural Reinforcement and Antimicrobial Properties, Macromolecular Bioscience, 2008, 8, 932-941.

NanoHorizons, Product Data Sheet, SmartSilver® ACM-5, Product # NP10-SX09-M, Oct. 15, 2012.

\* cited by examiner

*Primary Examiner* — Blessing M Fubara
(74) *Attorney, Agent, or Firm* — Pepper Hamilton LLP

(57) ABSTRACT

An absorbent wound dressing comprises a hydrophilic porous substrate and polymer-stabilized silver nanoparticles distributed throughout the porous substrate. The silver nanoparticles have a particle size $d_{50}$ in the range of about 45 nm to about 85 nm and the silver nanoparticles are present in the substrate in an amount of about 0.16% to about 1.5% by weight of the total weight of the substrate. The wound dressing produces a 7-day log reduction of 4 or more for bacteria in accordance with the Modified AATCC Test Method 100. The wound dressing is also non-cytotoxic in accordance with ISO 10993-5 standard procedure for medical device cytotoxicity assessment.

15 Claims, No Drawings

ANTI-MICROBIAL FOAMS CONTAINING POLYMER-STABILIZED SILVER NANOPARTICLES

CROSS-REFERENCE TO RELATED APPLICATIONS

This application claims the benefit under 35 U.S.C. §119 (e) of U.S. Provisional Application No. 62/036,672, filed Aug. 13, 2014, the entire contents of which are incorporated by reference as if fully set forth herein.

FIELD OF THE INVENTION

This invention relates to anti-microbial wound dressings and, more particularly, to anti-bacterial and anti-fungal porous substrates or foams for use in the treatment of exudate wounds.

BACKGROUND

Wound care dressings come in a variety of forms and are typically selected based on the nature and severity of the wound to be treated.

The management of wound exudates and prevention of infection present significant challenges. If a wound dressing does not adequately absorb and contain exudates, the moisture may cause skin maceration. Alginate and hydrofiber dressings, for example, absorb exudate and form a gel-like covering over the wound. Foam dressings absorb exudate and some lock fluid within the core of the dressing while others may transform into a gelling foam. Foam dressings may take on a broad range of physical characteristics based on the synthetic route selected to produce the foam which, in turn, can affect its ability to retain and release desired therapeutic agents, such as anti-bacterial and/or anti-fungal agents.

Silver is a known anti-microbial agent and is also provided in a wide variety of forms that can differ vastly with respect to their anti-microbial (e.g., anti-bacterial and/or anti-fungal) efficacy and cytotoxicity. There is ongoing debate as to the safety of silver when it is systemically absorbed through the wound. Moreover, silver has a tendency to precipitate into a salt and cause undesired discoloration. There has been ongoing work in providing silver in a form that is stable, retains its anti-microbial efficacy for an extended period of time and is non-cytotoxic to permit cell growth required for healing.

What is therefore desired is an improved wound dressing that can adequately absorb wound exudates and maintain its anti-microbial efficacy at the wound site for a desired period of time, while at the same time remaining non-cytotoxic so as to promote new cell growth and healing.

BRIEF SUMMARY

In one embodiment, an absorbent wound dressing is provided. The wound dressing comprises a hydrophilic porous substrate and polymer-stabilized silver nanoparticles distributed throughout the porous substrate. The silver nanoparticles have a particle size $d_{50}$ in the range of about 45 nm to about 85 nm and the silver nanoparticles are present in the substrate in an amount of about 0.16% to about 1.5% by weight of the total weight of the substrate. The wound dressing produces a 7-day log reduction of 4 or more for bacteria in accordance with the Modified AATCC Test Method 100. The wound dressing is also non-cytotoxic in accordance with ISO 10993-5 standard procedure for medical device cytotoxicity assessment.

In a first aspect, the silver nanoparticles are present in an amount from about 0.75% to about 1.5% by weight of the substrate.

In a second aspect, the wound dressing further comprises one or a combination of polyhexamethylene biguanide (PHMB) and chlorhexidine gluconate (CHG).

In a third aspect, the polymer-stabilized silver nanoparticles are distributed substantially uniformly throughout the substrate.

In a fourth aspect, the hydrophilic porous substrate comprises open-celled windows and closed-celled windows.

In a fifth aspect, the wound dressing produces a 24-hour log reduction of 2 or more for fungal species. The fungal species can be *Candida albicans*.

In a sixth aspect, the wound dressing produces a 7-day log reduction of 4 or more for gram-negative bacteria. The gram-negative bacterial can be *Pseudomonas aeruginosa* and/or *Klebsiella pneumoniae*.

In a seventh aspect, the wound dressing produces a 7-day log reduction of 4 or more for gram-positive bacteria. The gram-positive bacteria can be *Staphylococcus aureus*.

In another embodiment, a method for preparing a wound dressing is provided. The method comprises mixing a prepolymer and an aqueous solution comprising an aqueous dispersion of polymer-stabilized silver nanoparticles in deionized water to produce a polyurethane emulsion. The method further comprises curing the polyurethane emulsion to produce a three-dimensional, porous substrate having the polymer-stabilized silver nanoparticles distributed throughout the substrate.

In a first aspect, the prepolymer comprises an isocyanate-capped polyether.

In a second aspect, the prepolymer comprises an isocyanate-capped polyester.

In a third aspect, the polymer-stabilized silver nanoparticles have a particle size $d_{50}$ of about 45 nm to about 85 nm.

In a fourth aspect, the silver nanoparticles are present in an amount from about 0.16% to about 2.0% by weight of the substrate.

In a fifth aspect, the silver nanoparticles are present in an amount from about 0.75% to about 1.5% by weight of the substrate.

In a sixth aspect, the aqueous dispersion further comprises one or a combination of PHMB and CHG.

In a seventh aspect, the method further comprises providing the polyurethane emulsion between casting liners to a desired thickness and width before the curing.

In an eighth aspect, the polyurethane emulsion is dispensed into a three-dimensional mold to form a desired three-dimensional configuration before the curing.

In a ninth aspect, the method further comprises drying the three-dimensional, porous substrate.

In a tenth aspect, the polymer-stabilized silver nanoparticles are distributed substantially uniformly throughout the substrate.

In an eleventh aspect, the three-dimensional, porous substrate is produced without catalysts.

In a further embodiment, a method for preparing a wound dressing is provided. The method comprises mixing a polyisocyanate component and a hydrophilic polyol component comprising an aqueous dispersion of polymer-stabilized silver nanoparticles in deionized water to produce a polyurethane emulsion. The method further comprises curing the polyurethane emulsion in a desired three-dimensional configuration to produce a porous substrate having the polymer-stabilized silver nanoparticles distributed throughout the substrate.

In a first aspect, the polymer-stabilized silver nanoparticles have a particle size $d_{50}$ of about 45 nm to about 85 nm.

In a second aspect, the silver nanoparticles are present in an amount from about 0.16% to about 2.0% by weight of the substrate.

In a third aspect, the silver nanoparticles are present in an amount from about 0.75% to about 1.5% by weight of the substrate.

In a fourth aspect, the aqueous dispersion further comprises one or a combination of PHMB or CHG.

In a fifth aspect, the method further comprises providing the polyurethane emulsion between casting liners to a desired thickness and width before the curing.

In a sixth aspect, the polyurethane emulsion is dispensed into a three-dimensional mold to form a desired three-dimensional configuration before the curing.

In a seventh aspect, the method further comprises drying the three-dimensional, porous substrate.

In an eighth aspect, the polymer-stabilized silver nanoparticles are distributed substantially uniformly throughout the substrate.

In a ninth aspect, the three-dimensional, porous substrate is produced without catalysts.

In yet a further embodiment, a method of treating a wound in a patient is provided. The method comprises dressing the wound with an absorbent wound dressing. The absorbent wound dressing comprises a hydrophilic porous substrate and polymer-stabilized silver nanoparticles distributed throughout the porous substrate. The silver nanoparticles have a particle size $d_{50}$ in the range of about 45 nm to about 85 nm and the silver nanoparticles are present in the substrate in an amount of about 0.16% to about 1.5% by weight of the total weight of the substrate. The wound dressing produces a 7-day log reduction of 4 or more for bacteria in accordance with the Modified AATCC Test Method 100. The wound dressing is non-cytotoxic in accordance with ISO 10993-5 standard procedure for medical device cytotoxicity assessment.

In a first aspect, the silver nanoparticles are present in an amount from about 0.75% to about 1.5% by weight of the substrate.

In a second aspect, the wound dressing further comprises one or a combination of polyhexamethylene biguanide (PHMB) and chlorhexidine gluconate (CHG).

In a third aspect, the polymer-stabilized silver nanoparticles are distributed substantially uniformly throughout the substrate.

In a fourth aspect, the hydrophilic porous substrate comprises open-celled windows and closed-celled windows.

In a fifth aspect, the wound dressing produces a 24-hour log reduction of 2 or more for fungal species. The fungal species can be *Candida albicans*.

In a sixth aspect, the wound dressing produces a 7-day log reduction of 4 or more for gram-negative bacteria. The gram-negative bacterial can be *Pseudomonas aeruginosa* and/or *Klebsiella pneumoniae*.

In a seventh aspect, the wound dressing produces a 7-day log reduction of 4 or more for gram-positive bacteria. The gram-positive bacteria can be *Staphylococcus aureus*.

Other objects, features and advantages of the described preferred embodiments will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE EXEMPLARY EMBODIMENTS

Specific, non-limiting embodiments of the present invention will now be described with reference to the drawings. It should be understood that such embodiments are by way of example only and merely illustrative of but a small number of embodiments within the scope of the present invention. Various changes and modifications obvious to one skilled in the art to which the present invention pertains are deemed to be within the spirit, scope and contemplation of the present invention as further defined in the appended claims.

The absorbent wound care dressings described herein provide superior absorption and management of exudates while at the same time maintaining anti-microbial efficacy for an extended time period. Embodiments of the absorbent wound care dressings described herein maintain their anti-microbial efficacy for 24 hours or more, 3 days or more and 7 days or more as evidenced by at least a 4-log reduction of bacterial species, including gram-positive and gram-negative species. The anti-microbial efficacy has also been demonstrated for fungal species for at least 24 hours as evidenced by an at least a 2-log reduction of the fungal species. The prolonged anti-microbial efficacy owes to the chemical and physical characteristics of the polymer-stabilized silver nanoparticles, the hydrophilic foam substrate, and the manner in which the polymer-stabilized nanoparticles are incorporated within a hydrophilic porous substrate in synthesizing the wound dressing. The anti-microbial efficacy is also maintained by providing a controlled and relatively slow release of silver ions from the foam substrate and into the wound. The wound care dressings are also non-cytotoxic to promote cellular growth needed for wound healing.

Embodiments of the wound care dressings described herein generally comprise a hydrophilic porous substrate and polymer-stabilized silver nanoparticles distributed substantially uniformly throughout the substrate. In one embodiment, the silver may be provided in a non-ionic or metallic form. In another embodiment, the silver is not provided in a salt form. In a further embodiment, at least some of the non-ionic or metallic silver may be ionized or may be converted into an ionic form when it is in contact with the exudate environment.

The hydrophilic porous substrate or foam substrate described herein can refer to any absorbent, three-dimensional cellular polymeric material containing gas-filled voids. In certain embodiments, the foam excludes any fibrous or woven material. The foam can be substantially or entirely open-celled, closed-celled, have open-celled windows, have closed-cell windows, or have any combination of the foregoing.

In certain embodiments, the foam may be produced without the use of any catalysts. Such catalysts include tin and amine catalysts that are commonly used in the synthesis of polyurethanes, such as dibutyltin dilaurate, dibutyltin diacetate, stannous octoate, stannous octoate in dioctyl-phthalate, triethylene diamine in dipropylene glycol, bis (N,N dimethylaminoethyl) ether in dipropylene glycol. Thus, in certain embodiments, the foam substrates and the polymer-stabilized silver nanoparticle foams may be produced without employing any of the foregoing catalysts.

The foam substrates may be designed to absorb exudates when applied to the wound and also to slowly release metallic silver, silver ions or a combination of the two into the wound.

In one embodiment, the polymer-stabilized silver nanoparticle foams may be synthesized by reacting or mixing an isocyanate-capped prepolymer with an aqueous component to produce a polyurethane emulsion. It is understood that isocyanate-capped prepolymer includes isocyanate-terminated prepolymers and isocyanate end-capped prepolymers. In one embodiment, the synthesis of the polymer-stabilized silver nanoparticle foams does not require catalysts or other agents that may be cytotoxic or otherwise not biocompatible. In another embodiment, the synthesis of the polymer-stabilized silver nanoparticle foams exclude anti-microbial agents not described herein.

The isocyanate-terminated prepolymer can have an isocyanate content of about 1%, of about 2%, of about 3%, of about 4%, of about 5%, of about 6%, of about 7%, of about 8%, of about 9%, of about 10%, of about 11%, of about 12%, of about 13%, of about 14%, and of about 15%, and any range of the foregoing values. In one preferred embodiment, the prepolymer has an isocyanate content of about 6% to about 7% and in another embodiment, the prepolymer has an isocyanate content of about 9% to about 10%. The isocyanate-terminated prepolymer may be a polyether- or polyester-based prepolymer. The isocyanate-terminated prepolymer may also be a commercially available prepolymer, such as those available under the Pre'Pol brand (Essentra Porous Technologies, Richmond, Va.), including HI-LINK™ and OPTIPOL®, Hypol® (Dow Chemical Company), and Trepol® (Rynel, Inc.), to name a few.

The aqueous component comprises a colloidal aqueous dispersion that contains the polymer-stabilized pure metallic silver nanoparticles in Type II deionized water ($>1M'\Omega*cm$). Suitable commercially available polymer-stabilized silver nanoparticles include SmartSilver® ACM-5 (NanoHorizons, Inc., Bellefonte, Pa.). The amount of the polymer-stabilized silver nanoparticles provided in the aqueous component depends on the desired amount % by weight of silver that is desired for the resulting foam and can be calculated easily based on the desired amount of silver in the foam.

In one embodiment, the mixing ratio of the aqueous component to the prepolymer component may be about 0.5, about 0.6, about 0.7, about 0.8, about 0.9, about 1.0, about 1.1, about 1.2, about 1.3, about 1.4, about 1.5, about 1.6, about 1.7, about 1.8, about 1.9, about 2.0, about 2.1, about 2.2, about 2.3, about 2.4, and about 2.5. The mixing ratio can also be provided in a range of including and between any two of the foregoing values such as, for example, about 0.5 to about 2.5, about 0.5 to about 1.1, about 0.6 to about 1.0, and about 0.7 to about 0.9. In one embodiment, the mixing ratio may be about 0.8 (e.g., 80 parts aqueous component: 100 parts prepolymer component). This mixing ratio produces a foam substrate within a range of the physical properties, such as density (lbs/ft$^3$), tensile strength (psi), elongation at break (%), tear strength (lbs/in), absorption rate (sec.), free swell absorptive capacity (g/g), volume expansion (%), and fluid retention under 40 mm Hg compression (g/g).

The density (lbs/ft$^3$) of the resulting polymer-stabilized silver nanoparticle foams may preferably be at least about 2.50 lbs/ft$^3$, at least about 2.75 lbs/ft$^3$, at least about 3.00 lbs/ft$^3$, at least about 3.25 lbs/ft$^3$, at least about 3.50 lbs/ft$^3$, at least about 3.75 lbs/ft$^3$, at least about 4.00 lbs/ft$^3$, at least about 4.25 lbs/ft$^3$, at least about 4.50 lbs/ft$^3$, at least about 4.75 lbs/ft$^3$, at least about 5.00 lbs/ft$^3$, at least about 5.25 lbs/ft$^3$, at least about 5.50 lbs/ft$^3$, at least about 5.75 lbs/ft$^3$, at least about 6.00 lbs/ft$^3$, at least about 6.25 lbs/ft$^3$, at least about 6.50 lbs/ft$^3$, at least about 6.75 lbs/ft$^3$, at least about 7.00 lbs/ft$^3$, at least about 7.25 lbs/ft$^3$, at least about 7.50 lbs/ft$^3$, at least about 7.75 lbs/ft$^3$, at least about 8.00 lbs/ft$^3$, at least about 8.25 lbs/ft$^3$, at least about 8.50 lbs/ft$^3$, at least about 8.75 lbs/ft$^3$, at least about 9.00 lbs/ft$^3$, at least about 9.25 lbs/ft$^3$, at least about 9.50 lbs/ft$^3$, at least about 9.75 lbs/ft$^3$, at least about 10.00 lbs/ft$^3$, at least about 10.25 lbs/ft$^3$, at least about 10.50 lbs/ft$^3$, at least about 10.75 lbs/ft$^3$, at least about 11.00 lbs/ft$^3$, at least about 11.25 lbs/ft$^3$, at least about 11.50 lbs/ft$^3$, at least about 11.75 lbs/ft$^3$, at least about 12.00 lbs/ft$^3$, and in a range that includes and is between any two of the foregoing values.

The tensile strength (psi) of the resulting polymer-stabilized silver nanoparticle foams may preferably be at least about 5 psi, at least about 10 psi, at least about 15 psi, at least about 20 psi, at least about 25 psi, at least about 30 psi, at least about 35 psi, at least about 40 psi, at least about 45 psi, at least about 50 psi, and in a range that includes and is between any two of the foregoing values. In one embodiment, the tensile strength may be from about 10% to about 15%.

The elongation at break (%) of the resulting polymer-stabilized silver nanoparticle foams may preferably be at least about 100%, at least about 125%, at least about 150%, at least about 175%, at least about 200%, at least about 225%, at least about 250%, at least about 275%, at least about 300%, in a range that includes and is between any two of the foregoing values.

The tear strength (lbs/in) of the resulting polymer-stabilized silver nanoparticle foams may preferably be at least about 1.00 lbs/in, at least about 1.25 lbs/in, at least about 1.50 lbs/in, at least about 1.75 lbs/in, at least about 2.00 lbs/in, at least about 2.25 lbs/in, at least about 2.50 lbs/in, at least about 2.75 lbs/in, at least about 3.00 lbs/in, at least about 3.25 lbs/in, and in a range that includes and is between any two of the foregoing values.

The free swell absorptive capacity (g/g) of the resulting polymer-stabilized silver nanoparticle foams may preferably be at least about 5 g/g, at least about 10 g/g, at least about 15 g/g, at least about 20 g/g, and in a range that includes and is between any two of the foregoing values.

The volume expansion (%) of the resulting polymer-stabilized silver nanoparticle foams may preferably be at least about 50%, at least about 55%, at least about 60%, at least about 65%, at least about 70%, at least about 75%, at least about 80%, at least about 85%, at least about 90%, at least about 95%, at least about 100%, at least about 105%, at least about 110%, and in a range that includes and is between any two of the foregoing values.

The fluid retention under 40 mm Hg compression (g/g) of the resulting polymer-stabilized silver nanoparticle foams may preferably be at least about 5 g/g, at least about 6 g/g, at least about 7 g/g, at least about 8 g/g, at least about 9 g/g, at least about 10 g/g, at least about 11 g/g, at least about 12 g/g, at least about 13 g/g, at least about 14 g/g, at least about 15 g/g, and including and in a range that includes and is between any two of the foregoing values.

The resulting foam substrate may comprise any one or a combination of open cells, closed cells, partially open cells, partially closed cells, open-celled windows, and closed-celled windows. Open cell and open-celled windows create foams contain pores that are connected to each other and form an interconnected network that is relatively soft that will fill with whatever they are surrounded with. Closed-celled foams typically have higher compressive strength due to their structure. They have higher dimensional stability, low moisture absorption coefficient and higher strength.

The polymer-stabilized silver nanoparticle foam may also be produced by what is known as a "one-shot" method which comprises mixing a polyisocyanate component (i.e., an isocyanate having two or more reactive isocyanate group) or a prepolymer (as previously described) with a hydrophilic polyol component in the presence of foam-forming agents to produce a polyurethane emulsion. Exemplary polyisocyanates include toluene diisocyanate (TDI), 4,4'-dipheynyl-methane diisocyanate (MDI), dicyclohexylmethane-4,4'-diisocyanate ($H_{12}MDI$), hexamethylene diisocyanate (HDI) and variants thereof. The hydrophilic polyol component comprises the colloidal aqueous dispersion that contains the polymer-stabilized pure metallic silver nanoparticles. In one embodiment, the one-shot method may be performed without the use of a catalyst to produce the polymer-stabilized nanoparticle foam. In another embodiment, the one-shot method is performed using a small amount of an amine catalyst or an alternate catalyst that is not amine-based.

The polyurethane emulsion can then be cured to produce a three-dimensional, porous substrate having the polymer-stabilized silver nanoparticles distributed substantially uniformly throughout the substrate. The polyurethane emulsion may then be poured onto and sandwiched between casting liners. The casting liners may be removed at the end of the production line before the foam is dried and cured. The dried and cured foam may be ultimately obtained as rolled goods with thickness ranging from about 1 mm to about 5 inches. The desired thickness and the width of the resulting foams can be adjusted by adjusting the process conditions. Alternatively, the polyurethane emulsion may also be formed into a three-dimensional porous substrate by molding, in which the polyurethane emulsion may be dispensed into a mold and cured in an oven.

Polymer-stabilized silver nanoparticles can refer to silver nanoparticles which are directly or indirectly associated with one or more polymers so as to provide stabilization of the silver nanoparticles in the colloid solution and to prevent agglomeration or binding of the nanoparticles together to make larger particles. Polymer-stabilized silver nanoparticles may be provided in an aqueous colloidal solution, such as SmartSilver® ACM-5 (NanoHorizons, Inc., Bellefonte, Pa.).

In one embodiment, the polymer-stabilized silver nanoparticles can be polymer-coated silver nanoparticles. In another embodiment, the polymer-stabilized silver nanoparticles can be silver nanoparticles, which are at least partially, if not completely, encapsulated within polymer coatings. In a further embodiment, the polymer-stabilized silver nanoparticles can include surface-functionalized silver nanoparticles, which are directly or indirectly associated with a polymer through covalent or other bonding.

Exemplary polymers used in stabilizing, coating and/or encapsulating the silver nanoparticles include, for example, polyvinylpyrrolidone (PVP), polyvinyl alcohol (PVA), methacrylate/polystyrene copolymers, and other suitable polymers or co-polymers.

The particle sizes and amounts of the silver nanoparticles may be optimized to provide anti-microbial efficacy over a broad range of bacteria and fungi at lower amounts.

The particle size values provided below may reflect the particle sizes for the silver nanoparticles without the polymer and for the polymer-stabilized silver nanoparticles, i.e., for the polymer-coated or encapsulated silver nanoparticles.

The particle sizes of the silver nanoparticles or the polymer-stabilized silver nanoparticles may preferably be about 100 nm or less. In one embodiment, the particle sizes or the average particle sizes of the silver nanoparticles or the polymer-stabilized silver nanoparticles may be in the range of from about 30 nm to about 100 nm.

The particle sizes of the silver nanoparticles or the polymer-stabilized silver nanoparticles can also be characterized with reference to particle size distribution, with $d_{50}$ representing the median value in which half of the particles have diameters above and half of the particles have diameters below the median value, $d_{10}$ representing the value in which in which 10% of the particles have a smaller diameters than the stated value and 90% of the particles have larger diameters than the stated value, and $d_{90}$ representing the value in which in which 90% of the particles have a smaller diameters than the stated value and 10% of the particles have larger diameters than the stated value.

In one embodiment, the silver nanoparticles or the polymer-stabilized silver nanoparticles can have a $d_{50}$ value of about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, about 45 nm, about 46 nm, about 47 nm, about 48 nm, about 49 nm, about 50 nm, about 51 nm, about 52 nm, about 53 nm, about 54 nm, about 55 nm, about 56 nm, about 57 nm, about 58 nm, about 59 nm, about 60 nm, about 61 nm, about 62 nm, about 63 nm, about 64 nm, about 65 nm, about 66 nm, about 67 nm, about 68 nm, about 69 nm, about 70 nm, about 71 nm, about 72 nm, about 73 nm, about 74 nm, about 75 nm, about 76 nm, about 77 nm, about 78 nm, about 79 nm, about 80 nm, about 81 nm, about 82 nm, about 83 nm, about 84 nm, about 85 nm, about 86 nm, about 87 nm, about 88 nm, about 89 nm, about 90 nm, about 91 nm, about 92 nm, about 93 nm, about 94 nm, and about 95 nm. In another embodiment, the silver nanoparticles or the polymer-stabilized silver nanoparticles can have a $d_{50}$ value that is in the range of including and between any two of the foregoing values.

In another embodiment, the silver particles or the polymer-stabilized silver nanoparticles can have a $d_{10}$ value of about 25 nm, about 26 nm, about 27 nm, about 28 nm, about 29 nm, about 30 nm, about 31 nm, about 32 nm, about 33 nm, about 34 nm, about 35 nm, about 36 nm, about 37 nm, about 38 nm, about 39 nm, about 40 nm, about 41 nm, about 42 nm, about 43 nm, about 44 nm, and about 45 nm. In another embodiment, the silver nanoparticles or the polymer-stabilized silver nanoparticles can have a $d_{10}$ value that is in the range of including and between any two of the foregoing values.

In a further embodiment, the silver nanoparticles or the polymer-stabilized silver nanoparticles can have a $d_{90}$ value of about 85 nm, about 86 nm, about 87 nm, about 88 nm, about 89 nm, about 90 nm, about 91 nm, about 92 nm, about 93 nm, about 94 nm, about 95 nm, about 96 nm, about 97 nm, about 98 nm, about 99 nm, and about 100 nm. In another embodiment, the silver nanoparticles or the polymer-stabilized silver nanoparticles can have a $d_{50}$ value that is in the range of including and between any two of the foregoing values.

It is understood that the silver nanoparticles or the polymer-stabilized silver nanoparticles can have any combination of the foregoing $d_{50}$, $d_{10}$, and $d_{90}$ values.

The amount of silver nanoparticles that can be present in the wound dressing can range from about x to about y % by weight of the substrate. The values for x and y can be chosen from any of the following values so long as y>x: 0.10, 0.11, 0.12, 0.13, 0.014, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40, 0.41, 0.42, 0.43, 0.44, 0.45, 0.46, 0.47, 0.48, 0.49, 0.50, 0.51, 0.52, 0.53, 0.54, 0.55, 0.56, 0.57, 0.58, 0.59, 0.60, 0.61, 0.62, 0.63, 0.64, 0.65, 0.66, 0.67, 0.68, 0.69, 0.70, 0.71, 0.72, 0.73, 0.74, 0.75, 0.76, 0.77, 0.78, 0.79, 0.80, 0.81, 0.82, 0.83, 0.84, 0.85, 0.86, 0.87, 0.88, 0.89, 0.90, 0.91, 0.92, 0.93, 0.94, 0.95, 0.96, 0.97, 0.98, 0.99, 1.00, 1.01, 1.02, 1.03, 1.04, 1.05, 1.06, 1.07, 1.08, 1.09, 1.10, 1.11, 1.12, 1.13, 1.14, 1.15, 1.16, 1.17, 1.18, 1.19, 1.20, 1.21, 1.22, 1.23, 1.24, 1.25, 1.26, 1.27, 1.28, 1.29, 1.30, 1.31, 1.32, 1.33, 1.34, 1.35, 1.36, 1.37, 1.38, 1.39, 1.40, 1.41, 1.42, 1.43, 1.44, 1.45, 1.46, 1.47, 1.48, 1.49, 1.50, 1.51, 1.52, 1.53, 1.54, 1.55, 1.56, 1.57, 1.58, 1.59, 1.60, 1.61, 1.62, 1.63, 1.64, 1.65, 1.66, 1.67, 1.68, 1.69, 1.70, 1.71, 1.72, 1.73, 1.74, 1.75, 1.76, 1.78, 1.79, 1.80, 1.81, 1.82, 1.83, 1.84, 1.85, 1.86, 1.87, 1.88, 1.89, 1.90, 1.91, 1.92, 1.93, 1.94, 1.95, 1.96, 1.97, 1.98, 1.99, and 2.00. In one embodiment, the amount of silver nanoparticles can be present in an amount of from about 0.16% to about 1.5% by weight of the substrate. In another embodiment, the amount of silver nanoparticles can be present in an amount of from about 0.75% to about 1.50% weight by weight of the substrate.

In one embodiment, the weight of the substrate can be based on the weight of the substrate when it is in a hydrated state. The substrate can comprise less than about 10%, about 9%, about 8%, about 7%, about 6%, about 5%, about 4%, about 3%, about 2%, about 1%. about 0.75%, about 0.50%, about 0.25%, and about 0.10% water by weight of the substrate.

In another embodiment, the weight of the substrate can be based on the weight of the substrate when it is in a substantially dry or completely dry state. It is understood that "substantially dry" and "completely dry" does not completely exclude the presence of water or the ambient humidity in the environment.

In one embodiment, it is understood that when the term "about" precedes a specific value, it defines a range from 90% of the specific value to 110% of the specific value such that, for example, "about 2.00" would define a range from 1.80 to 2.20. In another embodiment, when the term "about" precedes a specific value, it defines a range from 80% of the specific value to 120% of the specific value such that, for example, "about 2.00" would define a range from 1.60 to 2.40. In a further embodiment, when the term "about" precedes a specific value, it defines a range from 70% of the specific value to 130% of the specific value such that for example, "about 2.00" would define a range from 1.40 to 2.60.

The polymer-stabilized silver nanoparticle described herein may be incorporated in and within a porous substrate or a foam in a form and amount that will optimize the anti-microbial activity with respect to one or more types of bacteria and fungi. The anti-microbial efficacy can be reflected in the percent or logarithmic reduction ("log reduction"). The log reduction that reflects anti-microbial efficacy can be obtained by way of a Modified AATCC Test Method 100 and the values can be taken at various time intervals after initial inoculation to after 24 hours, after 3 days and after 7 days.

In one embodiment, the anti-microbial efficacy, over an effective anti-microbial duration, is at least about a 2.00 log reduction, at least about a 2.25 log reduction, at least about a 2.50 log reduction, at least about a 2.75 log reduction, at least about a 3.00 log reduction, at least about a 3.25 log reduction, at least about a 3.50 log reduction, at least about a 3.75 log reduction, at least about a 4.00 log reduction, at least about a 4.25 log reduction, at least about a 4.50 log reduction, at least about a 4.75 log reduction, at least about a 5.00 log reduction, at least about a 5.25 log reduction, at least about a 5.50 log reduction, at least about a 5.75 log reduction, at least about a 6.00 log reduction, at least about a 6.25 log reduction, at least about a 6.50 log reduction, at least about a 6.75 log reduction, at least about a 7.00 log reduction, at least about a 7.25 log reduction, at least about a 7.50 log reduction, at least about a 7.75 log reduction, and at least about an 8.00 log reduction.

The foregoing log reductions can be maintained over an effective anti-microbial duration. The effective anti-microbial duration can be at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, and at least 31 days. The effective anti-microbial duration can be in a range that includes and is between any two of the foregoing values.

The anti-microbial efficacy may be maintained by providing a controlled and relatively slow release of metallic silver, silver ions or both from the foam substrate and into the wound. The controlled and relatively slow release of metallic silver, silver ions or both may be provided by virtue of the manner in which the polymer-stabilized silver nanoparticles may be incorporated and distributed in the foam substrate during the synthesis of the foam substrate. In one embodiment, the metallic silver may be encapsulated in a polymer and contact with the wound exudate releases the metallic silver from the polymer encapsulation and into the wound, in the metallic form or in the ionic form.

The values for log reduction that reflect anti-microbial efficacy can be provided for specific types of bacteria, including gram-negative bacteria, such as *Pseudomonas aeruginosa* and/or *Klebsiella pneumoniae*, gram-positive bacteria, such as *Staphylococcus aureus*. The values for log reduction that reflect anti-microbial efficacy can be provided for specific types of fungi, such as *Candida albicans*. It is understood that different log reduction values may be provided for different types of bacteria and fungi.

Exemplary gram-negative bacteria include *Escherichia coli* (*E. coli*), *Salmonella*, *Shigella*, and other Enterobacteriaceae, *Pseudomonas, Moraxella, Helicobacter, Stenotrophomonas, Bdellovibrio*, acetic acid bacteria, *Legionella*, cyanobacteria, spirochaetes, green sulfur, green non-sulfur bacteria, *Neisseria gonorrhoeae, Neisseria meningitides, Moraxella catarrhalis, Hemophilus influenzae, Klebsiella pneumoniae, Legionella pneumophila, Pseudomonas aeruginosa, Proteus mirabilis, Enterobacter cloacae, Serratia marcescens, Helicobacter pylori, Salmonella enteritidis, Salmonella typhi,* and *Acinetobacter baumannii*.

Exemplary gram-positive bacteria include *Streptococcus, Staphylococcus, Corynebacterium, Listeria, Bacillus, Clostridium, Rathybacter, Leifsonia,* and *Clavibacter.*

Exemplary fungi include *Aspergillus, Blastomyces dermatitidis, Candida albicans, Coccidioides, Cryptococcus neoformans, Cryptococcus gattii, Histoplasma capsulatum, Mucoromycotina, Pneumocystis jirovecii*, ringworm, *Sporothrix schenckii, Cladosporium,* and *Exserohilum.*

The anti-microbial efficacy can be enhanced synergistically by the inclusion of one or a combination of polyhexamethylene biguanide (PHMB) and chlorhexidine gluconate (CHG), which is a polymer that can be used as a disinfectant and antiseptic.

PHMB is believed to be effective against *Pseudomonas aeruginosa, Staphylococcus aureus, Escherichia coli, Candida albicans, Aspergillus brasiliensis*, vancomycin-resistant enterococci, and *Klebsiella pneumoniae*, among others. PHMB is believed to work by binding to bacterial cell membrane, causing complex reactions to alter the integrity of the cell membrane wall. This allows entry of PHMB, reducing wall strength and hence, death of the bacterium.

CHG is an anti-septic anti-bacterial agent. It is positively charged and reacts with the negatively charged microbial cell surface, thereby destroying the integrity of the cell membrane. Subsequently, chlorhexidine gluconate penetrates into the cell and causes leakage of intracellular components leading to cell death. Since gram-positive bacteria are more negatively charged, they are more sensitive to this agent.

In one embodiment, the polymer-stabilized silver nanoparticle foams may further comprise one or a combination of PHMB and CHG. In one embodiment, one or both of PHMB and CHG may be associated with or bound to the silver nanoparticles. In another embodiment, one or both of PHMB and CHG may each be associated with or bound to the foam substrate. In either of these embodiments, one or both of PHMB and/or CHG may be provided in an amount of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, and about 2.0% by weight of the foam substrate. In another embodiment, one or both of PHMB and CHG may be provided in an amount of less than about 10%, less than about 9%, less than about 8%, less than about 7%, less than about 6%, less than about 5%, less than about 4%, less than about 3%, less than about 2%, and less than about 1% by weight of the foam substrate. In a further embodiment, either one or both of PHMB and CHG may be provided in a range that includes and is between two of the foregoing values.

Preferred embodiments of the polymer-stabilized silver nanoparticle foams described herein are additionally demonstrated to be non-cytotoxic in accordance with ISO 10993-5. Example 2 compares the cytotoxicity of the polymer-stabilized silver nanoparticle foams described herein with commercially available silver wound dressings, with the polymer-stabilized silver nanoparticle foams having average cytotoxicity scores of 2 or less as compared with the commercially available silver wound dressings, which have average cytotoxicity scores of greater than 2. In one embodiment, the polymer-stabilized nanoparticle foams have a cytotoxicity score of 2 or less, 1 or less or 0 and are therefore considered non-cytotoxic in accordance with ISO 10993-5. In one embodiment, the polymer-stabilized silver nanoparticle foams do not include any additional components which are known to be anti-bacterial, anti-fungal, and/or cytotoxic, other than the components described herein.

Example 1

Preparation of the Anti-Bacterial/Anti-Fungal Foams

Hydrophilic polyurethane foams having a thickness of 5.0±0.5 mm were prepared with varying amounts of the polymer-stabilized silver nanoparticles as described herein.

An isocyanate-terminated prepolymer was mixed with an aqueous component comprising a predetermined amount of the polymer-stabilized silver nanoparticle dispersion in deionized water. The resultant mixture or polyurethane emulsion was dispensed onto a moving bottom casting liner of the production line and sandwiched between a moving top casting liner. The top and bottom casting liners were removed at the end of the production line after the foam material is tack-free. The foam material can then be dried in an oven or similar device.

In X80244, the aqueous component was prepared to produce a form that comprised 0.16% of polymer-stabilized silver nanoparticles in the dry foam. The aqueous component was mixed with an isocyanate-terminated prepolymer having an isocyanate content in the range of about 9% to about 10%. In X80245, CJNB#9-50(3), CJNB#9-52(3), CJNB#9-64, and CJNB#9-76, the same process was used, with the exception that the isocyanate-terminated prepolymer had an isocyanate content of about 6% to about 7%. The resulting polyurethane was poured onto the bottom casing liner and cast between top and bottom casting liners as described above.

The physical and absorbent characteristics are set forth in Table 1 below:

TABLE 1

Physical and Absorbent Characteristics of Polymer-Stabilized Silver Nanoparticle Foams.

| PROPERTY | X80244 0.16% nanosilver in dry foam | X80245 0.18% nanosilver in dry foam | CJNB #9-50(3) 0.75% nanosilver in dry foam | CJNB #9-52(3) 1.5% nanosilver in dry foam | CJNB #9-64 1.25% nanosilver in dry foam |
|---|---|---|---|---|---|
| Density (lbs/ft$^3$) | 4.92 | 6.09 | 6.46 | 6.76 | 6.92 |
| Tensile Strength (psi) | 46.23 | 13.25 | 12.33 | 14.59 | 15.46 |
| Elongation at Break (%) | 177 | 273 | 243 | 276 | 269 |
| Tear Strength (lbs/in) | 3.12 | 1.90 | 1.99 | 2.08 | 1.98 |
| Absorption Rate of a Water Drop (sec) | 1 | 1 | 1 | 1 | 1 |
| Free Swell Absorptive Capacity (g/g) | 18.9 | 17.6 | 16.62 | 16.28 | 16.8 |
| Volume Expansion (%) | 65 | 86 | 88 | 95 | 101 |
| Fluid Retention Under 40 mm Hg Compression (g/g) | 11.41 | 9.98 | 9.72 | 10.15 | 10.04 |

Physical characteristics were measured as per ASTM standard D3574.

Absorption rate of a water drop is the time to absorb a drop of water into foam substrate. The anti-microbial foams described herein take about 1 sec to absorb a drop of water into foam substrate indicating instantaneous absorption/wicking rate.

Absorptive capacity of the foam is measured as per British Standard, BS EN 13726-1:2002, Test methods for primary wound dressings—Part 1: Aspects of Absorbency, Section 3.2: Free swell absorptive capacity. As shown in the results, the foam substrates can absorb 16-19 times of its own weight when in contact with a saline solution with the volume expansion of the foam from 65-to slightly over 100%. High absorptive capacity is advantageous as it would absorb exudates and move fluid away from the wound/skin interface towards the dressing layer.

Fluid retention under compression of 40 mm Hg pressure indicates the typical compression created by a bandage when wrap around the wound dressing. Results indicate that even under compression of 40 mm Hg pressure, foam still keeps a larger amount of exudate trapped inside the foam (without releasing back to wound bed) providing faster healing through exudate management.

Anti-microbial agents can be provided or incorporated in the foam substrates described herein to control the wound bioburden in critical colonization and local infection.

Example 2

In Vitro Cytotoxicity Tests

A Minimal Essential Media (MEM) elution test was performed to determine the cytotoxicity of extractable substances. An extract of the test article was added to cell monolayers and incubated. The cell monolayers were examined and scored based on the degree of cellular destruction. All test method acceptance criteria were met. Testing was performed in compliance with U.S. FDA good manufacturing practice regulations 21 CFR Parts 210, 211 and 820.

Procedure.

The amounts of test article and controls extracted were based on ANSI/AAMI/ISO and USP surface area or weight recommendations. Test articles and controls were extracted in 1×MEM with 5% bovine serum for 24-25 hours at 37±1° C. with agitation. Multiple well cell culture plates were seeded with a verified quantity of industry standard L-929 cells (AC CCL-1) and incubated until approximately 80% confluent. The test article and control extracts were held at room temperature for less than four hours before testing. The extract fluids were not filtered, centrifuged or manipulated in any way following the extraction process. The test article and control extracts were added to the cell monolayers in triplicate. The cells were incubated at 37±1° C. with 5±1% $CO_2$ for 48±3 hours.

Acceptance Criteria.

The United States Pharmacopeia & National Formulary (USP <87>) states that the test article meets the requirements, or receives a passing score (Pass) if the reactivity grade is not greater than 2 or a mild reactivity. The ANSI/AAMI/ISO 10993-5 standard states that the achievement of a numerical grade greater than 2 is considered a cytotoxic effect, or a failing score (Fail).

TABLE 2

Culture Scores.

| Conditions of All cultures | Reactivity | Score |
| --- | --- | --- |
| No cell lysis, intracytoplastic granules | None | 0 |
| Less than or equal to 20% rounding, occasional lysed cells | Slight | 1 |
| Greater than 20% to less than or equal to 50% rounding, no extensive cell lysis | Mild | 2 |
| Greater than 50% to less than 70% rounding and lysed cell | Moderate | 3 |
| Nearly complete destruction of the cell layers | Severe | 4 |

The acceptance criteria was based upon the negative and media controls receiving "0" reactivity grades and the positive controls receiving a 3-4 reactivity grades (moderate to severe). The test was considered valid as the control results were within acceptable parameters.

TABLE 3

Negative, Media and Positive Control Scores.

| Controls | Scores | | | | Extraction Ratio | Amt. Tested/ Extraction Solvent Amt. |
| --- | --- | --- | --- | --- | --- | --- |
| | #1 | #2 | #3 | Avg. | | |
| Negative Control—polypropylene pellets | 0 | 0 | 0 | 0 | 0.2 g/ml | 4 g/20 ml |
| Media Control | 0 | 0 | 0 | 0 | N/A | 20 ml |
| Positive Control—Latex Natural Rubber | 4 | 4 | 4 | 4 | 0.2 g/ml | 4.0 g/20 ml |

The cell monolayers were examined microscopically. The wells were scored as to the degree of discernable morphological cytotoxicity on a relative scale of 0 to 4.

TABLE 4

In vitro Cytotoxicity Test Scores.

| Test Article | Scores | | | | Result | Extraction Ratio | Amt. Tested/ Extraction Solvent Amt. |
| --- | --- | --- | --- | --- | --- | --- | --- |
| | #1 | #2 | #3 | Avg. | | | |
| 3M Tegaderm ® AG Silver Sulfate Mesh 2 in. × 2 in. | 4 | 4 | 4 | 4 | Fail | 0.1 g/ml | 0.6 g/6 ml |
| Contreet ® AG Silver Foam Dressing, 4 in. × 4 in. | 3 | 3 | 3 | 3 | Fail | 0.1 g/ml | 2.0 g/20 ml |
| Acticoat ® Absorbent w/ avec Silcryst ® Nanocrystals 4 in. × 5 in. | 4 | 4 | 4 | 4 | Fail | 0.1 g/ml | 2.0 g/20 ml |
| Acticoat ® Flex 3 w/ avec. Silcryst ® Nanocrystals 2 in. × 2 in. | 4 | 4 | 4 | 4 | Fail | 0.1 g/ml | 0.9 g/9.0 ml |
| Mepilex ® Ag with Safetac ® Technology, 4 in. × 4 in. | 4 | 4 | 4 | 4 | Fail | 0.1 g/ml | 2.0 g/20 ml |
| Essentra 0.17% nanosilver in dry foam CJNB#9-24C | 0 | 0 | 0 | 0 | Pass | 0.1 g/ml | 2.0 g/20 ml |
| Essentra 1.25% nanosilver in dry foam CJNB#9-64 | 2 | 2 | 2 | 2 | Pass | 0.1 g/ml | 2.0 g/20 ml |

TABLE 4-continued

In vitro Cytotoxicity Test Scores.

| Test Article | Scores | | | | Re-sult | Extrac-tion Ratio | Amt. Tested/ Extraction Solvent Amt. |
|---|---|---|---|---|---|---|---|
| | #1 | #2 | #3 | Avg. | | | |
| Essentra 1.5% nanosilver in dry foam CJNB#9-70 | 0 | 0 | 1 | 0 | Pass | 0.1 g/ml | 2.0 g/20 ml |
| Essentra 1.5% Nanosilver in dry foam CJNB#9-71 | 1 | 1 | 0 | 1 | Pass | 0.1 g/ml | 2.0 g/20 ml |

Example 3

In Vitro Anti-Bacterial Tests for X80244 and X80245

The anti-bacterial activity of X80244 and X80245 foams was tested and compared to control foams. The anti-microbial performance of each foam was assessed using the Modified American Association of Textile Colorist and Chemist (AATCC) Test Method 100.

At day zero, samples were prepared and placed in a small Petri dish, which was then placed in a large Petri dish with 10 ml of sterile water to keep the samples in a humid condition. Plates were labeled with sample identification, time point and organism name. Each challenge organism was adjusted to $1-5 \times 10^6$ CFU/ml using a spectrophotometer (*Staphylococcus aureus* (ATCC 25922 or equivalent), *Klebsiella pneumoniae* (ATCC 4352 or equivalent), *Pseudomonas aeruginosa* (ATCC 9027 or equivalent).

Zero hour samples were inoculated with 1.0 ml of the challenge organism and immediately neutralized with 100 ml of D/E neutralizing broth and appropriate dilutions were made with sterile saline and each dilution was plated in duplicate. Plates were incubated for 24-48 hours at $37 \pm 2^\circ$ C. Twenty-four hour samples were individually inoculated with 1.0 ml of the specified population of the challenge organism, while two sets of 3 day and 7 day samples (one set for zero hour and one set for 24 hour) were conditioned with 0.1 ml of 10% fetal bovine serum (FBS) in sterile deionized water. Samples were then incubated at $37 \pm 2^\circ$ C.

After 24 hours of incubation, 24 hour samples were removed, neutralized with 100 ml of neutralizer and appropriate dilutions were made with sterile saline and each dilution was plated in duplicate. The 3 and 7 day samples were conditioned with 0.1 ml of 10% FBS each day and aged at $37 \pm 2^\circ$ C. until the testing point. At 3 day and 7 day time point a new set of inoculum was prepared and each sample was inoculated with the specified population of challenge organism. One set of samples was inoculated, immediately neutralized and plated for zero hour. A second set was inoculated and placed in the incubator at $37 \pm 2^\circ$ C. for 24 hours.

After incubation, each sample was individually neutralized with 100 ml of neutralizer. Appropriate dilutions were made with sterile saline and each dilution was plated in duplicate.

TABLE 5

Anti-Bacterial Results after 24 hours.

| Sample ID | Zero time | 24 Hour | Log Reduction | Percent Reduction |
|---|---|---|---|---|
| *S. aureus* | | | | |
| X80245 Silver 0.18% silver | $1.85 \times 10^6$ | $4.40 \times 10^4$ | 2.83 | 99.85 |
| Control | $2.35 \times 10^6$ | $>3.00 \times 10^7$ | No Reduction | No Reduction |
| X80244 Silver 0.16% silver | $2.15 \times 10^6$ | $5.85 \times 10^4$ | 2.71 | 99.81 |
| Control | $1.95 \times 10^6$ | $>3.00 \times 10^7$ | No Reduction | No Reduction |
| *K. pneumoniae* | | | | |
| X80245 Silver 0.18% silver | $1.95 \times 10^6$ | $5.00 \times 10^1$ | 5.78 | 99.99 |
| Control | $2.20 \times 10^6$ | $>3.00 \times 10^7$ | No Reduction | No Reduction |
| X80244 Silver 0.16% silver | $1.95 \times 10^6$ | $6.90 \times 10^2$ | 4.64 | 99.99 |
| Control | $1.85 \times 10^6$ | $>3.00 \times 10^7$ | No Reduction | No Reduction |
| *P. aeruginosa* | | | | |
| X80245 Silver 0.18% silver | $2.10 \times 10^6$ | $<1.00 \times 10^1$ | >6.48 | >99.99 |
| Control | $2.30 \times 10^6$ | $>3.00 \times 10^7$ | No Reduction | No Reduction |
| X80244 Silver 0.16% silver | $2.10 \times 10^6$ | $4.80 \times 10^3$ | 3.80 | 99.98 |
| Control | $1.90 \times 10^6$ | $>3.00 \times 10^7$ | No Reduction | No Reduction |

The polymer-stabilized silver nanoparticle foam having 0.16% and 0.18% of silver nanoparticles by weight of the foam demonstrated 24-hour log reductions of 2.71 and 2.83 for *S. aureus*, log reductions of 4.64 and 5.78 for *K. pneumoniae*, and log reductions of 3.80 and >6.48 for *P. aeruginosa*.

TABLE 6

Anti-Bacterial Results after 3 Days.

| Sample ID | Zero time | 3 Day | Log Reduction | Percent Reduction |
|---|---|---|---|---|
| *S. aureus* | | | | |
| X80245 Silver 0.18% silver | $1.50 \times 10^6$ | $6.65 \times 10^3$ | 3.65 | 99.98 |
| Control | $2.50 \times 10^6$ | $>3.00 \times 10^7$ | No Reduction | No Reduction |
| X80244 Silver 0.16% silver | $2.35 \times 10^6$ | $3.25 \times 10^4$ | 2.97 | 99.89 |
| Control | $1.80 \times 10^6$ | $>3.00 \times 10^7$ | No Reduction | No Reduction |
| *K. pneumoniae* | | | | |
| X80245 Silver 0.18% silver | $2.20 \times 10^6$ | $<1.00 \times 10^1$ | >6.48 | >99.99 |
| Control | $2.40 \times 10^6$ | $>3.00 \times 10^7$ | No Reduction | No Reduction |
| X80244 Silver 0.16% silver | $2.35 \times 10^6$ | $5.15 \times 10^4$ | 2.77 | 99.83 |
| Control | $1.60 \times 10^6$ | $>3.00 \times 10^7$ | No Reduction | No Reduction |
| *P. aeruginosa* | | | | |
| X80245 Silver 0.18% silver | $1.40 \times 10^6$ | $<1.00 \times 10^1$ | >6.48 | >99.99 |
| Control | $1.90 \times 10^6$ | $>3.00 \times 10^7$ | No Reduction | No Reduction |
| X80244 Silver 0.16% silver | $1.55 \times 10^6$ | $3.30 \times 10^5$ | 1.96 | 98.90 |
| Control | $2.45 \times 10^6$ | $>3.00 \times 10^7$ | No Reduction | No Reduction |

The polymer-stabilized silver nanoparticle foam having 0.16% and 0.18% of silver nanoparticles by weight of the foam demonstrated 3-day log reductions of 2.97 and 3.65 for *S. aureus*, log reductions of 2.77 and >6.48 for *K. pneumoniae*, and log reductions of 1.96 and >6.48 for *P. aeruginosa*.

TABLE 7

Anti-Bacterial Results after 7 Days.

| Sample ID | Zero time | 7 Day | Log Reduction | Percent Reduction |
|---|---|---|---|---|
| *S. aureus* | | | | |
| X80245 Silver 0.18% silver | $1.75 \times 10^6$ | $2.50 \times 10^4$ | 4.89 | 99.99 |
| Control | $1.75 \times 10^6$ | $1.95 \times 10^9$ | No Reduction | No Reduction |
| X80244 Silver 0.16% silver | $1.85 \times 10^6$ | $3.80 \times 10^4$ | 5.12 | 99.99 |
| Control | $2.00 \times 10^6$ | $5.00 \times 10^9$ | No Reduction | No Reduction |
| *K. pneumoniae* | | | | |
| X80245 Silver 0.18% silver | $1.20 \times 10^6$ | $1.65 \times 10^5$ | 3.80 | 99.98 |
| Control | $1.25 \times 10^6$ | $1.05 \times 10^9$ | No Reduction | No Reduction |
| X80244 Silver 0.16% silver | $1.65 \times 10^6$ | $3.05 \times 10^4$ | 5.19 | 99.99 |
| Control | $1.75 \times 10^6$ | $4.75 \times 10^9$ | No Reduction | No Reduction |
| *P. aeruginosa* | | | | |
| X80245 Silver 0.18% silver | $1.65 \times 10^6$ | $2.65 \times 10^5$ | 6.57 | 99.99 |
| Control | $1.75 \times 10^6$ | $9.80 \times 10^{11}$ | No Reduction | No Reduction |
| X80244 Silver 0.16% silver | $1.95 \times 10^6$ | $1.75 \times 10^8$ | 3.17 | 99.93 |
| Control | $1.85 \times 10^6$ | $2.60 \times 10^{11}$ | No Reduction | No Reduction |

The polymer-stabilized silver nanoparticle foam having 0.16% and 0.18% of silver nanoparticles by weight of the foam demonstrated 7-day log reductions of 5.12 and 4.89 for *S. aureus*, log reductions of 5.19 and 3.8 for *K. pneumoniae*, and log reductions of 3.17 and 6.57 for *P. aeruginosa*.

Example 4

In Vitro Anti-Bacterial Tests for CJNB#9-50(3) and CJNB#9-52(3)

The anti-bacterial activity of hydrophilic foams utilizing different amounts of silver nanoparticles were also compared using the same protocol as described above with respect to Example 3. The test samples (CJNB#9-50(3) and CJNB#9-52(3)) contained an amount of silver at 0.75% and 1.5% by weight of the dry foam, respectively.

TABLE 8

Anti-Bacterial Results after 24 hours.

Results (CFU/sample)

| Day—0 Sample ID | Zero Contact Time | | 24 Hour Contact Time | | Percent Reduction/Log Reduction | |
|---|---|---|---|---|---|---|
| | *S. aureus* | *K. pneumoniae* | *S. aureus* | *K. pneumoniae* | *S. aureus* | *K. pneumoniae* |
| Control | $1.34 \times 10^6$ | $1.56 \times 10^6$ | $7.65 \times 10^6$ | $8.70 \times 10^6$ | Not Applicable | Not Applicable |
| CJNB#9-50(3) 0.75% Ag | $1.65 \times 10^6$ | $1.35 \times 10^6$ | $7.45 \times 10^2$ | $<1.00 \times 10^1$ | 99.99/ 4.01 | >99.99/ >5.94 |
| CJNB#9-52(3) 1.5% Ag | $1.50 \times 10^6$ | $1.25 \times 10^6$ | $<1.00 \times 10^1$ | $<1.00 \times 10^1$ | >99.99/ >5.88 | >99.99/ >5.94 |
| | *P. aeruginosa* | | *P. aeruginosa* | | *P. aeruginosa* | |
| Control | $1.06 \times 10^6$ | | $3.95 \times 10^6$ | | Not Applicable | |
| CJNB#9-50(3) 0.75% Ag | $1.45 \times 10^6$ | | $<1.00 \times 10^1$ | | >99.99/ >5.60 | |
| CJNB#9-52(3) 1.5% Ag | $1.40 \times 10^6$ | | $<1.00 \times 10^1$ | | >99.99/ >5.60 | |

After 24 hours, the polymer-stabilized silver nanoparticle foam having 0.75% by weight of foam of silver nanoparticles demonstrated 24-hour log reductions of about 4.01 for *S. aureus*, >5.94 for *K. pneumoniae*, and >5.60 for *P. aeruginosa*. The polymer-stabilized silver nanoparticle foam having 1.50% by weight of foam of silver nanoparticles demonstrated 24-hour log reductions of about 5.88 for *S. aureus*, >5.94 for *K. pneumoniae*, and >5.60 for *P. aeruginosa*.

TABLE 9

Anti-Bacterial Results after 3 Days.

Results (CFU/sample)

| Day—3 Sample ID | Zero Contact Time | | 24 Hour Contact Time | | Percent Reduction/Log Reduction | |
|---|---|---|---|---|---|---|
| | *S. aureus* | *K. pneumoniae* | *S. aureus* | *K. pneumoniae* | *S. aureus* | *K. pneumoniae* |
| Control | $1.40 \times 10^6$ | $1.55 \times 10^6$ | $2.30 \times 10^7$ | $2.55 \times 10^8$ | Not Applicable | Not Applicable |

TABLE 9-continued

Anti-Bacterial Results after 3 Days.

Results (CFU/sample)

| Day—3 | Zero Contact Time | | 24 Hour Contact Time | | Percent Reduction/Log Reduction | |
|---|---|---|---|---|---|---|
| CJNB#9-50(3) 0.75% Ag | $2.20 \times 10^6$ | $2.20 \times 10^6$ | $<1.00 \times 10^1$ | $<1.00 \times 10^1$ | >99.99/ >6.36 | >99.99/ >7.41 |
| CJNB#9-52(3) 1.5% Ag | $2.00 \times 10^6$ | $1.50 \times 10^6$ | $<1.00 \times 10^1$ | $<1.00 \times 10^1$ | >99.99/ >6.36 | >99.99/ >7.41 |

| | *P. aeruginosa* | *P. aeruginosa* | *P. aeruginosa* |
|---|---|---|---|
| Control | $2.20 \times 10^6$ | $2.55 \times 10^8$ | Not Applicable |
| CJNB#9-50(3) 0.75% Ag | $1.75 \times 10^6$ | $<1.00 \times 10^1$ | >99.99/ >7.41 |
| CJNB#9-52(3) 1.5% Ag | $2.60 \times 10^6$ | $<1.00 \times 10^1$ | >99.99/ >7.41 |

After 3 days, the polymer-stabilized silver nanoparticle foam having 0.75% by weight of foam of silver nanoparticles demonstrated 3-day log reductions of about >6.36 for *S. aureus*, >7.41 for *K. pneumoniae*, and >7.41 for *P. aeruginosa*. The polymer-stabilized silver nanoparticle foam having 1.50% by weight of foam of silver nanoparticles demonstrated 3-day log reductions of about >6.36 for *S. aureus*, >7.41 for *K. pneumoniae*, and >7.41 for *P. aeruginosa*.

TABLE 10

Anti-Bacterial Results after 7 Days.

Results (CFU/sample)

| Day—7 | Zero Contact Time | | 24 Hour Contact Time | | Percent Reduction/Log Reduction | |
|---|---|---|---|---|---|---|
| Sample ID | *S. aureus* | *K. pneumoniae* | *S. aureus* | *K. pneumoniae* | *S. aureus* | *K. pneumoniae* |
| Control | $2.80 \times 10^6$ | $2.85 \times 10^6$ | $1.89 \times 10^8$ | $1.31 \times 10^9$ | Not Applicable | Not Applicable |
| CJNB#9-50(3) 0.75% Ag | $2.85 \times 10^6$ | $2.60 \times 10^6$ | $3.65 \times 10^2$ | $<1.00 \times 10^1$ | >99.99/ 5.71 | >99.99/ >8.12 |
| CJNB#9-52(3) 1.5% Ag | $2.80 \times 10^6$ | $2.45 \times 10^6$ | $<1.00 \times 10^1$ | $<1.00 \times 10^1$ | >99.99/ >7.28 | >99.99/ >8.12 |

| | *P. aeruginosa* | *P. aeruginosa* | *P. aeruginosa* |
|---|---|---|---|
| Control | $2.85 \times 10^6$ | $4.05 \times 10^8$ | Not Applicable |
| CJNB#9-50(3) 0.75% Ag | $2.55 \times 10^6$ | $<1.00 \times 10^1$ | >99.99/ >7.61 |
| CJNB#9-52(3) 1.5% Ag | $2.35 \times 10^6$ | $<1.00 \times 10^1$ | >99.99/ >7.61 |

After 7 days, the polymer-stabilized silver nanoparticle foam having 0.75% by weight of foam of silver nanoparticles demonstrated 7-day log reductions of about 5.71 for *S. aureus*, >8.12 for *K. pneumoniae*, and >7.61 for *P. aeruginosa*. The polymer-stabilized silver nanoparticle foam having 1.50% by weight of foam of silver nanoparticles demonstrated 7-day log reductions of about >7.28 for *S. aureus*, >8.12 for *K. pneumoniae*, and >7.61 for *P. aeruginosa*.

Example 5

In Vitro Anti-Fungal Test for CJNB#9-52(3)

The anti-fungal activity of CJNB#9-52(3) (1.5% nanosilver in dry foam, 4-5 mm thickness) was tested and evaluated. Specified layers of sample were inoculated evenly with the challenge organism (*Candida albicans*). After inoculation, samples were incubated at 35-39° C. for 24 hours. Immediately after incubation, zero contact time samples were neutralized with D/E neutralizing broth. Serial dilutions were prepared and plated in duplicate using appropriate media. The 24 hour samples were processed similarly.

All plates were then incubated at 28±1° C. for 48 hours. The number of organisms per specimen was reported and the percent reduction and log reduction of challenge organisms were calculated.

TABLE 11

Anti-Fungal Activity after 24 Hours.

| | Results | | |
|---|---|---|---|
| Sample ID | Zero Contact Time CFU/specimen *C. albicans* | 24 hour Contact Time CFU/specimen *C. albicans* | % Reduction/Log Reduction *C. albicans* |
| CJNB#9-52(3) 1.5% nanosilver | $2.85 \times 10^6$ | $9.15 \times 10^3$ | 99.68/2.49 |

As demonstrated in table above, the nanosilver foam exhibited a 99.68% reduction or a 2.49 log reduction of *C. albicans* after 24 hours.

Example 6

The anti-bacterial activity of CJNB#9-40, which comprises 0.75% polymer-stabilized silver nanoparticles and 0.5% PHMB in dry polyurethane form, was assessed using the same protocol as described above with respect to Example 3.

TABLE 12

Anti-Bacterial Activity after 24 Hours.

| | Results (CFU/sample) | | | | | |
|---|---|---|---|---|---|---|
| Day—0 | Zero Contact Time | | 24 Hour Contact Time | | Percent Reduction/Log Reduction | |
| Sample ID | *S. aureus* | *K. pneumoniae* | *S. aureus* | *K. pneumoniae* | *S. aureus* | *K. pneumoniae* |
| Control | $1.34 \times 10^6$ | $1.55 \times 10^6$ | $7.65 \times 10^6$ | $8.70 \times 10^6$ | Not Applicable | Not Applicable |
| CJNB#9-40 | $1.50 \times 10^6$ | $1.45 \times 10^6$ | $<1.00 \times 10^1$ | $<1.00 \times 10^1$ | >99.99/ >5.88 | >99.99/ >5.94 |

| | *P. aeruginosa* | *P. aeruginosa* | *P. aeruginosa* |
|---|---|---|---|
| Control | $1.06 \times 10^6$ | $3.95 \times 10^6$ | Not Applicable |
| CJNB#9-40 | $1.35 \times 10^6$ | $<1.00 \times 10^1$ | >99.99/ >5.60 |

After 24 hours, CJNB#9-40 demonstrated 24-hour log reductions of about >5.88 for *S. aureus*, >5.94 for *K. pneumoniae* and >5.60 for *P. aeruginosa*.

TABLE 13

Anti-Bacterial Activity after 3 Days.

Results (CFU/sample)

| Day 3 Sample ID | Zero Contact Time | | 24 Hour Contact Time | | Percent Reduction/Log Reduction | |
|---|---|---|---|---|---|---|
| | S. aureus | K. pneumoniae | S. aureus | K. pneumoniae | S. aureus | K. pneumoniae |
| Control | $1.40 \times 10^6$ | $1.55 \times 10^6$ | $2.30 \times 10^7$ | $2.55 \times 10^8$ | Not Applicable | Not Applicable |
| CJNB#9-40 | $2.75 \times 10^6$ | $2.35 \times 10^6$ | $2.50 \times 10^2$ | $<1.00 \times 10^1$ | 99.99/ 4.96 | >99.99/ >7.40 |

| | P. aeruginosa | P. aeruginosa | P. aeruginosa |
|---|---|---|---|
| Control | $2.20 \times 10^6$ | $2.95 \times 10^8$ | Applicable |
| CJNB#9-40 | $2.55 \times 10^6$ | $<1.00 \times 10^1$ | >99.99/ >7.47 |

After 3 days, CJNB#9-40 demonstrated 3-day log reductions of about >4.96 for *S. aureus*, >7.40 for *K. pneumoniae* and >7.47 for *P. aeruginosa*.

TABLE 14

Anti-Bacterial Activity after 7 Days.

Results (CFU/sample)

| Day—7 Sample ID | Zero Contact Time | | 24 Hour Contact Time | | Percent Reduction/Log Reduction | |
|---|---|---|---|---|---|---|
| | S. aureus | K. pneumoniae | S. aureus | K. pneumoniae | S. aureus | K. pneumoniae |
| Control | $3.80 \times 10^6$ | $2.85 \times 10^6$ | $1.89 \times 10^8$ | $1.31 \times 10^9$ | Not Applicable | Not Applicable |
| CJNB#9-40 | $2.95 \times 10^6$ | $2.30 \times 10^6$ | $<1.00 \times 10^1$ | $<1.00 \times 10^1$ | 99.99/ >7.28 | >99.99/ >8.12 |

| | P. aeruginosa | P. aeruginosa | P. aeruginosa |
|---|---|---|---|
| Control | $2.85 \times 10^6$ | $4.05 \times 10^8$ | Not Applicable |
| CJNB#9-40 | $3.50 \times 10^6$ | $<1.00 \times 10^1$ | >99.99/ >7.61 |

After 7 days, CJNB#9-40 demonstrated 7-day log reductions of about >7.28 for *S. aureus*, >7.61 for *K. pneumoniae* and >8.12 for *P. aeruginosa*.

Example 7

In Vitro Anti-Bacterial Tests Comparing Silver Particle Sizes

The anti-bacterial activity of hydrophilic foams utilizing different silver particle sizes were also compared using the same protocol as described above with respect to Example 3. Each of the test samples (CJNB#9-76 and CJNB#9-52(3)) contained an amount of silver at 1.5% by weight of the dry foam.

TABLE 15

Anti-Bacterial Results for *S. aureus*.

| | Silver Particle Size | Zero Contact Time | 24 Hour Contact Time | Log Reduction |
|---|---|---|---|---|
| CJNB#9-76 | 15-25 microns | $2.95 \times 10^6$ | $3.60 \times 10^4$ | 1.91 |
| CJNB#9-52(3) | 30-100 nm | $1.50 \times 10^6$ | $<1.00 \times 10^1$ | >5.26 |

As can be seen in table above, the foam having the larger silver particle size (CJNB#9-76) had a 24-hour log reduction of 1.91 relative to the initial inoculum concentration of *S. aureus* as compared to the foam having the smaller silver particle size (CJNB#9-52(3)), which had a significantly larger 24-hour log reduction of >5.26 relative to the initial inoculum concentration for the same organism. The smaller particle size has significantly greater anti-bacterial efficacy as against *S. aureus*.

TABLE 16

Anti-Bacterial Results for *P. aeruginosa*.

| | Silver Particle Size | Zero Contact Time | 24 Hour Contact Time | Log Reduction |
|---|---|---|---|---|
| CJNB#9-76 | 15-25 microns | $1.71 \times 10^6$ | $28.35 \times 10^6$ | No reduction |
| CJNB#9-52(3) | 30-100 nm | $1.25 \times 10^6$ | $<1.00 \times 10^1$ | >5.30 |

As can be seen in table above, the foam having the larger silver particle size (CJNB#9-76) had no reduction relative to the initial inoculum concentration of *P. aeruginosa* as compared to the foam having the smaller silver particle size (CJNB#9-52(3)), which had a significantly larger 24-hour log reduction of >5.30 relative to the initial inoculum concentration for the same organism. The larger particle size is demonstrated here to have no anti-bacterial efficacy against *P. aeruginosa*, while the smaller particle size maintains a significant anti-bacterial efficacy.

TABLE 17

Anti-Bacterial Results for *K. pneumoniae*.

| | Silver Particle Size | Zero Contact Time | 24 Hour Contact Time | Log Reduction |
|---|---|---|---|---|
| CJNB#9-76 | 15-25 microns | $1.25 \times 10^6$ | $7.30 \times 102$ | 3.24 |
| CJNB#9-52(3) | 30-100 nm | $1.45 \times 10^6$ | $<1.00 \times 10^1$ | >5.32 |

As can be seen in table above, the foam having the larger silver particle size (CJNB#9-76) had a 24-hour log reduction of 3.24 relative to the initial inoculum concentration of *P. aeruginosa* as compared to the foam having the smaller silver particle size (CJNB#9-52(3)), which had a significantly larger 24-hour log reduction of >5.32 relative to the initial inoculum concentration for the same organism. The smaller particle size has significantly greater anti-bacterial efficacy as against *K. pneumoniae*.

It is to be understood that the detailed description and specific examples, while indicating preferred embodiments of the present disclosure, are given by way of illustration and not limitation. Many changes and modifications within the scope of the present disclosure may be made without departing from the spirit thereof, and the disclosure includes all such modifications.

The invention claimed is:

1. An absorbent wound dressing comprising:
   a hydrophilic porous substrate; and
   polymer-stabilized silver nanoparticles distributed throughout the porous substrate, the silver nanoparticles having a particle size $d_{50}$ in the range of about 45 nm to about 85 nm and the silver nanoparticles being present in the substrate in an amount of about 0.16% to about 1.5% by weight of the total weight of the substrate;
   wherein the wound dressing produces a 7-day log reduction of 4 or more for bacteria in accordance with the Modified AATCC Test Method 100;
   wherein the wound dressing is non-cytotoxic in accordance with ISO 10993-5 standard procedure for medical device cytotoxicity assessment; and
   wherein the hydrophilic porous substrate comprises open-celled windows and closed-celled windows.

2. The wound dressing of claim 1, wherein the silver nanoparticles are present in an amount from about 0.75% to about 1.5% by weight of the substrate.

3. The wound dressing of claim 1, further comprising one or a combination of polyhexamethylene biguanide (PHMB) and chlorhexidine gluconate (CHG).

4. The wound dressing of claim 1, wherein the polymer-stabilized silver nanoparticles are distributed substantially uniformly throughout the substrate.

5. The wound dressing of claim 1, wherein the wound dressing produces a 24-hour log reduction of 2 or more for fungal species.

6. The wound dressing of claim 1, wherein the wound dressing produces a 7-day log reduction of 4 or more for gram-negative bacteria.

7. The wound dressing of claim 1, wherein the wound dressing produces a 7-day log reduction of 4 or more for gram-positive bacteria.

8. The wound dressing of claim 1, wherein:
   the silver nanoparticles are present in an amount of 0.25% by weight of total weight of the hydrophilic porous substrate; and
   the hydrophilic porous substrate comprises polyhexamethylene biguanide (PHMB) in an amount of 1.00% by weight of the hydrophilic porous substrate.

9. The wound dressing of claim 1, wherein:
   the silver nanoparticles are present in an amount of about 0.75% by weight of total weight of the hydrophilic porous substrate; and
   the hydrophilic porous substrate comprises polyhexamethylene biguanide (PHMB) in an amount of about 0.50% by weight of the hydrophilic porous substrate.

10. The wound dressing of claim 1, wherein:
    the silver nanoparticles are present in an amount of 0.10% to about 2.00% by weight of the hydrophilic porous substrate; and the hydrophilic porous substrate comprises polyhexamethylene biguanide (PHMB) in an amount of about 0.10% to about 2.00% by weight of the hydrophilic porous substrate.

11. The wound dressing of claim 1, wherein:
the silver nanoparticles are present in an amount of about 0.10% to about 2.00% by weight of the total weight of the hydrophilic porous substrate;
the hydrophilic porous substrate comprises polyhexamethylene biguanide (PHMB) in an amount of about 0.10% to about 2.00% by weight of the hydrophilic porous substrate, and
the hydrophilic porous substrate comprises chlorhexidine gluconate (CHG) in an amount of about 0.10% to about 2.00% by weight of the hydrophilic porous substrate.

12. The wound dressing of claim 1, wherein:
the silver nanoparticles are present in an amount of about 0.10% by weight of the hydrophilic porous substrate; and
the hydrophilic porous substrate comprises polyhexamethylene biguanide (PHMB) in an amount of about 0.75% to about 1.50% by weight of the hydrophilic porous substrate.

13. The wound dressing of claim 1, wherein the hydrophilic porous substrate comprises a polyurethane foam.

14. An absorbent wound dressing comprising:
a hydrophilic porous substrate;
polymer-stabilized nanoparticles distributed throughout the porous substrate, wherein the nanoparticles are comprised of elemental silver;
polyhexamethylene biguanide (PHMB); and
chlorhexidine gluconate (CHG);
wherein the wound dressing produces a 7-day log reduction of 4 or more for bacteria in accordance with the Modified AATCC Test Method 100;
wherein the wound dressing is non-cytotoxic in accordance with ISO 10993-5 standard procedure for medical device cytotoxicity assessment; and
wherein the hydrophilic porous substrate comprises open-celled windows and closed-celled windows.

15. The wound dressing of claim 14, wherein the hydrophilic porous substrate comprises a polyurethane foam.

* * * * *